F. J. CURRAN

June 28, 1932. INSECTICIDE AND DEODORIZING TABLET Re. 18,504

Filed Aug. 17, 1928

Original Filed Aug. 17, 1928

Inventor:
Francis J. Curran.
By: Charles T. Wilson
Attys.

Reissued June 28, 1932

Re. 18,504

UNITED STATES PATENT OFFICE

FRANCIS J. CURRAN, OF CHICAGO, ILLINOIS

INSECTICIDE AND DEODORIZING TABLET

Original No. 1,803,238, dated April 28, 1931, Serial No. 300,225, filed August 17, 1928. Application for reissue filed April 27, 1932. Serial No. 609,002.

The invention relates to an insecticide and deodorizing tablet of the kind that is hung on the wall of a clothes closet and particularly to one so constructed that evaporation of the deodorant takes place uniformly throughout its entire surface, thus lengthening the usefulness of such an article.

I am aware that similar articles have heretofore been manufactured, but these are objectionable for the reason that the rear part of the deodorant body which rests against the wall does not evaporate. Evaporation of the tablets in use at the present time takes place in that part of the body in front of the board on which the deodorant is formed, so that when the front half is evaporated the device ceases to function and has to be discarded leaving substantially half of the deodorizing substance unevaporated on the back of the board.

My invention overcomes this objection in that the deodorant body is so formed on the board or support as to have knobs at the lower corners thereof, which knobs maintain the body out of contact with the wall, permitting circulation of air entirely about the body of the deodorant, resulting in uniform evaporation of the same, thus lengthening the usefulness of the article.

An object of the invention is to provide an insecticide and deodorizing tablet which will evaporate evenly and uniformly throughout its entire surface.

Another object is to provide such a tablet which is symmetrically disposed on a support or board, with knobs or shoulders which cooperate with the suspending connection for the tablet for keeping the body of the tablet away from the wall, thereby permitting uniform evaporation over the entire surface of the tablet.

Another object of the invention is to provide a tablet of the class described in which a roughened or absorbent board is used as the support on which the deodorant is formed.

A further object of the invention is to provide a deodorizing tablet which is economical to manufacture and which will evaporate uniformly about its entire surface.

The above, other and further objects of the invention will be apparent from the following description, accompanying drawing and appended claims.

According to the invention, the deodorizing tablet comprises a board of roughened or absorbent material on which the deodorant is symmetrically disposed by dipping the board into a mixture which solidifies on the board and in so solidifying assumes a substantially pyramidal shape in side elevation.

One form of the invention is illustrated in the accompanying drawing and the views thereof are as follows.

The form of the invention illustrated comprises a board or support 1 which has its surface roughened and which is made of absorbent material similar to blotting paper.

The body 2 of deodorant is formed on the board 1 by repeated dipping of the board into a mixture of substances used for providing a proper deodorant. The main substance employed for the deodorant is naphthalene which is tinted and perfumed.

The board 1 is repeatedly dipped into the mixture of the desired substances until the body 2 of deodorant is formed on the board of sufficient thickness as to provide a commercial article which will serve for a period of several months for the purposes intended.

Figure 1:
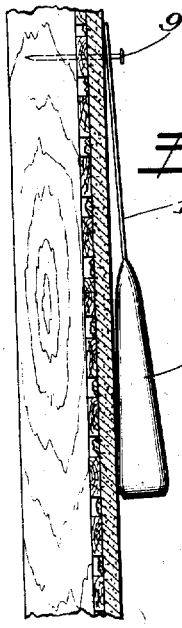
Figure 1 is a fragmental sectional view of a wall with a tablet embodying my invention suspended on the wall.
Figure 2:
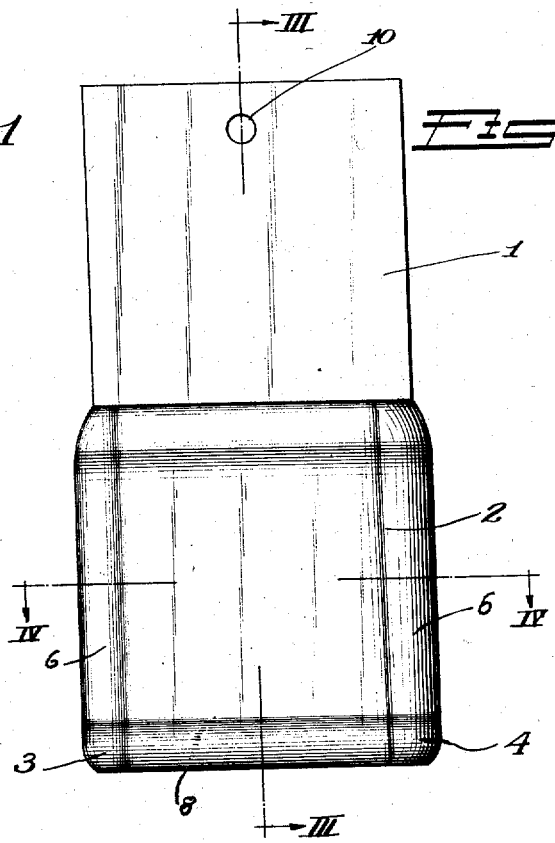
Figure 2 is a front elevational view of the tablet of Figure 1.
Figure 3:
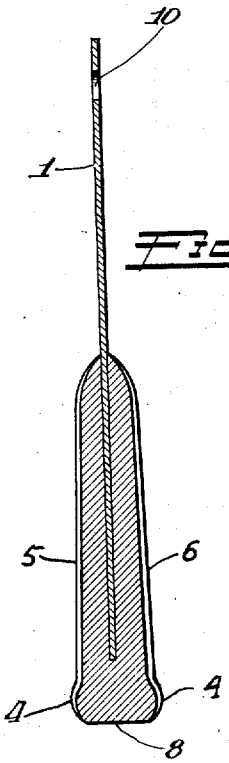
Figure 3 is a vertical section on line III—III of Figure 2.
Figure 4:
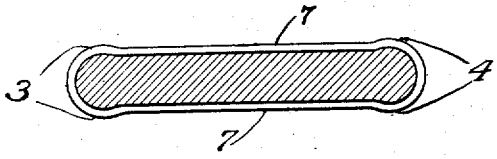
Figure 4 is a horizontal section on line IV—IV of Figure 2.

The deodorant substances in solidifying assume the shape of an inverted wedge as may be observed in Figures 1 and 3, with the widest part of the wedge at the bottom. Furthermore, the body of deodorant when solidified has shoulders or knobs 3 and 4 along the lower ends of the side surfaces of the body and marginal shoulders 5 and 6 along the sides of the body, with the walls 7 between these shoulders slightly depressed as shown clearly in Figures 3 and 4, thus forming projections or knobs at the corners.

The bottom 8 is trimmed so that no projections of the deodorant material remain on the finished article when the same has been fully formed.

The article is used in clothes closets, and the like, by being suspended against a wall of the closet on a nail, pin or hook 9 passing through an aperture 10 in the upper end of the body 1. When so suspended, the tablet will hang substantially in the position shown in Figure 1, that is with the knobs 3 and 4 against the wall, with the body of the tablet above such knobs out of contact with the wall, whereby air may circulate freely about such body thus causing uniform evaporation over its entire surface.

I have found that a deodorizing tablet constructed in accordance with this invention will outlast by some months the tablets in use at the present time and furthermore that a tablet of my invention will be completely evaporated on the back as well as the front of the board 1, thus utilizing every deodorizing effect possible in such device.

While I have described more or less precisely the details of construction of my invention, yet I do not wish to be understood as limiting myself thereto as I am aware that changes may be made in the arrangement and proportion of parts and that equivalents may be substituted, all without departing from the spirit and scope of my invention.

I claim as my invention:

1. A deodorizing tablet including a board coated uniformly on each side with a body formed of material which volatilizes slowly, the board being provided with means for suspending the same, said body having a marginal ridge about its lower end extending completely about said body, said body having enlargements at the lower corners thereof forming knobs for maintaining said body out of contact with a surface when said tablet is suspended on the same thereby allowing air circulation about the entire body above said shoulder for uniform evaporation.

2. A deodorizing tablet comprising a flat support having a portion for suspending said tablet and a body of deodorant adherent on said support surrounding the same below the suspending portion, said body having a ridge about its lower end and having enlargements at the lower corners thereof serving as knobs to maintain said body out of contact with a wall when said tablet is suspended on the wall.

3. A deodorizing tablet comprising a support having a portion for suspending said tablet, a body of deodorant adherent on said support below said suspending portion and completely surrounding the same, said body having a shoulder about its lower end of greater extent than the balance of said body and extending the full width of said body, said body having enlargements at the lower corners thereof forming knobs whereby said body is maintained out of contact with a wall when said tablet is hung thereon, the tablet having bearing contact with said wall only at the points of contact therewith of said knobs.

4. A deodorizing tablet comprising a flat support having a portion for suspending said tablet, a body of deodorant adherent thereon and surrounding said support, said body being transversely symmetrical about said support, said body having a shoulder about its lower end of greater extent than the balance of said body and extending the full width of said body, said body having enlargements at the corners thereof forming knobs whereby said body is maintained out of contact with a wall when said tablet is hung thereon, said tablet having bearing contact with a wall only at the points of contact between said knobs and the wall.

5. A deodorizing tablet comprising a roughened board having a portion for suspending said tablet, a body of deodorant adherent on said board being symmetrically formed thereon by dipping, said body being of progressively increasing thickness downwardly and terminating in a shoulder about its lower end and having enlargements at the lower corners thereof forming knobs, said knobs serving to maintain said body out of contact with a wall when hung on the same thereby permitting air circulation about the entire body for uniform evaporation.

6. A deodorizing tablet comprising a roughened board having a portion for suspending said tablet, a body of deodorant adherent on said board being symmetrically formed thereon by dipping, said body being of progressively increasing thickness downwardly and terminating in an enlargement at its lower end to maintain said body out of contact with a wall when hung on the same and to define a vertical ventilating space between said body and said wall thereby permitting air circulation about the entire body for uniform evaporation.

7. A deodorizing tablet comprising a flat support having a portion for suspending said tablet and a body of deodorant adherent on said support surrounding the same below the suspending portion, said body having a ridge about its lower end provided with an enlargement serving to maintain said body out of contact with a wall when said tablet is suspended on the wall so as to define a vertical ventilating space between the pad and said wall.

8. As an article of manufacture a deodorizing pad including a sheet and a deodorant solidified on both sides of said sheet and including a protuberance positioned so that when the pad is supported against a vertical flat surface it will define a vertical ventilating air space between itself and said surface.

9. In a deodorizing pad including a sheet and a deodorant solidified on both sides of said sheet to form a pad on said sheet, spacing means comprising a portion of said pad for defining a ventilating space between the upper and lower extremities of the deodorant pad and a vertical flat surface against which said pad may be supported.

In testimony whereof, I have hereunto subscribed my name at Chicago, Cook County, Illinois.

FRANCIS J. CURRAN.